(12) United States Patent
Cherian et al.

(10) Patent No.: US 6,608,050 B2
(45) Date of Patent: Aug. 19, 2003

(54) LYOPHILIZATE OF LIPID COMPLEX OF WATER INSOLUBLE PORPHYRINS

(75) Inventors: Mathew Cherian, Arese (IT); Shireesh Prakash Apte, Mansfield, TX (US)

(73) Assignee: Pharmacia & Upjohn Company, Kalamazoo, MI (US)

( * ) Notice: Subject to any disclaimer, the term of this patent is extended or adjusted under 35 U.S.C. 154(b) by 0 days.

(21) Appl. No.: 09/970,596

(22) Filed: Oct. 4, 2001

(65) Prior Publication Data

US 2002/0058643 A1 May 16, 2002

Related U.S. Application Data

(63) Continuation of application No. 09/778,279, filed on Feb. 7, 2001, now abandoned, and a continuation of application No. 09/341,932, filed as application No. PCT/US98/00033 on Jan. 23, 1998, now abandoned.

(51) Int. Cl.$^7$ .............................................. A61K 31/555
(52) U.S. Cl. ..................... 514/189; 514/188; 514/410; 514/427; 514/428; 514/429; 424/400; 424/499; 424/500; 556/81
(58) Field of Search ................................ 514/410, 189, 514/188, 427, 428, 429; 424/400, 499, 500

(56) References Cited

U.S. PATENT DOCUMENTS

| | | | |
|---|---|---|---|
| 5,277,913 A | | 1/1994 | Thompson et al. .......... 424/450 |
| 5,389,378 A | * | 2/1995 | Madden ........................ 514/410 |
| 5,707,608 A | * | 1/1998 | Liu et al. ..................... 424/9.61 |

FOREIGN PATENT DOCUMENTS

| | | | |
|---|---|---|---|
| EP | 0 569 113 A1 | | 11/1993 |
| EP | 0 720 853 A1 | | 7/1996 |
| GB | 720853 A1 | * | 12/1995 |
| WO | WO 96/32094 | | 10/1996 |
| WO | WO 96/32094 A1 | * | 10/1996 |
| WO | WO 97/04746 | | 2/1997 |

OTHER PUBLICATIONS

J.B. Cannon, "Pharmaceuticals and Drug Delivery Aspects of Heme and Porphyrin Therapy," *Journal of Pharmaceutical Sciences*, May, 1993, vol. 82, No. 5, pp. 435–446.*

Kuzelova, et al. "Interactions of Dicarboxylic Porphyrins with Unilamellar Lipidic Vesicles: Drastic Effects of pH and Cholesterol on Kinetics," *Biochemistry*, 1995, vol. 34, pp. 11245–11255.

Mayhew, et al. "Lipid–Associated Methylpheophorbide–A (Hexyl–Ether) as a Photodynamic Agent in Tumor–Bearing Mice," *Photochemistry and Photobiology*, 1993 vol. 58, No. 6, pp. 845–851.

Gregory, et al. "Interfacial Complexation of Phospholipid Langmuir Monolayers with Water–Soluble Porphyrins and Phthalocyanines: an X–ray Reflectivity Study," *Thin Solid Films*, 1996, vol. 284–285, pp. 849–853.

J.B. Cannon, "Pharmaceutics and Drug Delivery Aspects of Heme and Porphyrin Therapy," *Journal of Pharmaceutical Sciences* May, 1993, vol. 82, No. 5, pp. 435–446.

* cited by examiner

*Primary Examiner*—Dwayne C. Jones
(74) *Attorney, Agent, or Firm*—McDonnell Boehnen Hulbert & Berghoff

(57) ABSTRACT

The present invention relates to a pharmaceutically acceptable dosage form of water insoluble porphyrins, particularly metal containing porphyrins such as tin porphyrin, which can be complexed with a lipid, reconstituted from a lyophilizate and administrated to a patient in the treatment of cancer and other diseases.

16 Claims, No Drawings

LYOPHILIZATE OF LIPID COMPLEX OF WATER INSOLUBLE PORPHYRINS

This application is a continuation of U.S. application Ser. No. 09/778,279, filed Feb. 7, 2001, now abandoned, which is a continuation of U.S. application Ser. No. 09/341,932, filed Jul. 20, 1999, now abandoned, which is a 35 U.S.C. §371 of international application No. PCT/US98/00033, filed Jan. 23, 1998, which claims priority to U.S. application Ser. No. 08/789,566, filed Jan. 28, 1997, now abandoned.

BACKGROUND OF THE INVENTION

The present invention relates to a pharmaceutically acceptable dosage form of water insoluble porphyrins, particularly metal containing porphyrins such as tin porphyrin, which can be complexed with a lipid, reconstituted from a lyophilizate and administered to a patient in the treatment of cancer and other diseases.

Porphyrins are biologically active compounds, usually consisting of four pyrrole rings. Typically, they have a centrally located metal atom and are activated by light radiation of suitable wavelength. Porphyrins display antitumor activity in photodynamic therapy (PDT) where the porphyrins are administered to a patient and localize in neoplastic tissues. Typically, the neoplastic tissues are irradiated with light at a wavelength which corresponds to an absorption band of the porphyrin resulting in the activation of the porphyrin and preferential destruction of the neoplastic tissues. It has been suggested in U.S. Pat. No. 5,162,519 to Bonnett et al. that the mechanism involved is due to the production of the highly reactive singlet oxygen which is produced by transfer of energy from the light-excited porphyrin molecule to an oxygen molecule. Such photodynamic therapy is the subject of a series of articles making up a special issue of Photochemistry and Photobiology, Volume 46, number 5, November, 1987 (hereinafter "P&P 46-5"). According to these articles, photodynamic therapy has been used in the treatment of a wide variety of cancers including such solid tumors as cancers of the bronchial tubes, bladder, esophagus, lung, skin, head and neck, brain, and colon and intraocular and gynecologic cancers.

A major disadvantage to the use of porphyrins in the treatment of cancer is that when used in high concentrations to destroy the tumor cells, the porphyrins exhibit toxic side effects. The porphyrin is generally injected intravenously or intraperitoneally at a dose of about 2 mg per kg of body weight. At lower concentrations which might be more easily tolerated by the patient, the porphyrins tend to exhibit very little effect on the tumor cells.

It has been reported that porphyrins may be incorporated into a liposome and injected intraperitoneally. Spikes et al., "Photodynamic Behavior of Porphyrins in Model Cell, Tissue and Tumor Systems"; in Photodynamic Therapy of Tumors and Other Diseases (Edited by G. Jori and C. A. Perria); pages 45–53; Libreria Progetto, Padua (1985) and references cited therein.

There is a need for compositions containing porphyrins which are effective for the treatment of cancer and yet exhibit less toxic effects towards the patient.

SUMMARY OF THE INVENTION

It is an object of the present invention to provide a less toxic pharmaceutically acceptable dosage form of porphyrins for use in therapies such as chemotherapy and photodynamic therapy.

One manifestation of the present invention is complexes of a porphyrin and a phospholipid. Another manifestation of the invention is a lyophilizate of a complex of a porphyrin and a phospholipid, and a pharmaceutically acceptable excipient. Still another manifestation of the present invention is a method for preparing a lipid complex of a porphyrin.

The lipid complexes in accordance with this invention appear to be desirable for several reasons. It appears that the lipid complexes may sufficiently slow the release of the porphyrins that the porphyrins can be administered at higher dosage levels with less toxicity thereby improving treatment. The lipid complexes also appear to be more stable to ambient light and UV radiation than the porphyrin alone thus simplifying their handling. While it has not been confirmed, the lipid complexes may also preferentially accumulate in tumor tissues.

While the invention will hereafter be described with respect to the preparation of lipid complexes and lyophilizates of lipid complexes of tin porphyrin, those skilled in the art will appreciate that the methods taught herein are also applicable to the preparation of lipid complexes and lyophilizates of other porphyrins, particularly other metalloporphyrins.

In accordance with one embodiment of the invention, a lyophilizate of a phospholipid-porphyrin complex is prepared by a process comprising the steps of preparing a concentrated solution of a porphyrin and a phospholipid in an organic solvent, adding water to the solution to cause formation of a lipid complex of the porphyrin, removing the organic solvent to provide a dispersion of the lipid complex in water as an aqueous phase, dissolving a pharmaceutically acceptable excipient in the aqueous phase of the dispersion, and lyophilizing the dispersion of the lipid complex to form a lyophilizate.

In accordance with a preferred embodiment of the present invention, the lyophilizate is prepared by a method which comprises forming a concentrated solution of tin porphyrin and a mixture of dimyristoyl phosphatidylcholine (DMPC) and dimyristoyl phosphatidylglycerol (DMPG) in chloroform, adding an aqueous solution such as water for injection to form the lipid complex of tin porphyrin and provide a dispersion of the lipid complex in water as an aqueous phase, sparging the dispersion to remove the chloroform, reducing the particle size of the dispersion of the lipid complex, adding an aqueous solution of mannitol as a pharmaceutically acceptable lyophilization excipient to the dispersion, and lyophilizing the composition, wherein a lyophilizate is obtained which upon reconstituting with water provides a colloidal dispersion of a porphyrin-lipid complex. It is possible to prepare the solution of the prophyrin and the phospholipids by dissolving the porphyrin in one organic solvent, dissolving the phospholipids in another organic solvent, mixing the two solutions, and then removing the solvents after addition of water.

DETAILED DESCRIPTION OF THE INVENTION

The term "water insoluble porphyrin" as used herein means porphyrins having a solubility in water which is less than about 1.5 mg/ml at 23° C. and, more typically, is less than 0.5 mg/ml at 23° C. and still more typically less than 0.1 mg/ml at 23° C.

The term "lipid complex" is an art recognized term. Lipid complexes are characterized by a noncovalent bond between the lipid and the porphyrin which is observed by a phase change in differential scanning calorimetry. Liposomes are not lipid complexes within the meaning of the term.

The term "pharmaceutically acceptable aqueous diluent" as used herein refers to water for injection, saline, and other known aqueous vehicles.

The term "lyophilization excipient" refers to a substance which is added to a solution prior to lyophilization to enhance characteristics such as the color, texture, strength, and volume of the cake. Examples of lyophilization excipients are provided below.

The term "photodynamic therapy" (PDT) as used herein refers to a therapy treatment of a patient having a disease such as cancer wherein the patient is treated with a drug such as a porphyrin which has the tendency to preferentially accumulate in neoplastic tissues relative to normal tissues. The drug, when irradiated becomes toxic to the neoplastic tissue.

Porphyrins are biologically active nitrogen-containing compounds having a conjugated cyclic structure consisting of four pyrrole rings linked together through their 2- and 5-positions by methine bridges. The term "porphyrin" includes derivatives wherein a metal atom is chelated into the ring structure, presumably complexed or bonded to at least two of the nitrogens of the pyrrole ring. The metal atom inserted into the ring structure includes, e.g., tin, zinc, lanthanides, actinides, and those metals of the transition series of which chromium, manganese, iron, cobalt, nickel, and copper are exemplary. The preferred porphyrins for use in the present invention are metalloporphyrins, particularly tin porphyrins Tin porphyrin and other porphyrins useful in this invention are described in the literature. It is known to irradiate tumors and cancerous tissues in the human body with intensive light following administration of a hematoprophyrin derivative in the wavelength range of 626 to 636 nanometers to reduce and, at times, destroy the cancerous cells (see PCT published specification WO83/00811). It is also known that porphyrins, especially the sodium salt of protoporphyrins, can maintain or promote the normal functions of cells and are useful for preventing the genesis, growth, metastasis, and relapse of malignant tumors. Japanese Published Patent Application No. 125737/76 describes the use of porphyrins as tumor inhibiting agents, exemplifying etioporphyrin, mesoporphyrin, protoporphyrin, deuteroporphyrin, hematoporphyrin, coproporphyrin, and uroporphyrin. U.S. Pat. Nos. 4,837,221 and 5,162,519 to Bonnett et al. teach the therapy of tumors susceptible to necrosis by a porphyrin when adminstered to locate in the tumor and illuminated with light of a wavelength absorbed by the porphyrin. U.S. Pat. No. 5,512,559 to Shalkos et al describes the use of porphyrins and metal complexes of prophyrin in the photodynamic treatment of cancer tumors. European Patent Publication 0 186 962 describes therapy of tumors susceptible to necrosis when pharmacological acceptable meso-porphyrins are administered followed by illumination with light of a wavelength absorbed by the porphyrin.

U.S. Pat. No. 5,407,808, discloses hematoporphyrin derivatives or a mixture of porphyrins derived therefrom (e.g. Phyotofrin II), to mammalian tumor cells and then subject such cells to light of appropriate wavelength to effect cell destruction. Any porphyrin can be used in the present invention provided that it complexes with a phospholipid and is pharmaceutically active. Theoretically, any of these therapies could be modified by a lipid complex of the water insoluble porphyrins and administering it to the patient instead of the uncomplexed porphyrin. In order to produce the lipid complex and administer the complex as a colloidal dispersion in water, the porphyrin must be essentially water insoluble as defined above.

In accordance with the invention the porphyrin, particularly a tin porphyrin, is provided as a concentrated solution of the porphyrin in an organic solvent. The most typical example of the solvent used to prepare this solution is chloroform. However, other organic solvents such as methylene chloride, carbon tetrachloride, ethylene dichloride, freons, DMSO (dimethyl sulfoxide), DMA (dimethyl acetamide), etc. can be used. Useful solvents must form stable solutions with the porphyrin, e.g., the solvent must not interact with, destabilize, or deactivate the drug. In addition, the solubility of the porphyrin in the solvent must also be high enough that the porphyrin can be dissolved in amounts sufficiently high to form commercially useful quantities of the lipid complex, and the solvent should be capable of being removed easily from an aqueous dispersion of the lipid complex as described hereafter. Preferably, a solution having a concentration of about 0.25 to 25 mg/ml, preferably about 2 to 25 mg/ml and most preferably about 15 mg/ml porphyrin is used. The concentration may vary depending upon the nature of the solvent and temperature, but it is advantageous to use a concentrated solution of the porphyrin in preparing the lipid-porphyrin complex. This minimizes the amount of solvent that must be removed later in the process, and it also assists in forcing the porphyrin out of solution and into lipid porphyrin complex formation with the addition of water.

Typically, the phospholipids are dissolved separately. The organic solvent used to prepare the solution of the phospholipids should meet similar requirements to those outlined for the porphyrin solvent. It must be compatible with the phospholipids and not destabilize them or the porphyrins. In addition, the lipids should be soluble enough in the solvent so as to be able to introduce enough of the lipid to form the complex yet minimize the amount of solvent that must be removed later. A solvent which can be readily removed from the dispersion of the lipid complex is most preferred. The solvent most typically used to prepare this solution is chloroform or methylene chloride. Typically the concentration of this phospholipid solution will range from about 10 to 250 mg/ml. Preferably, the same solvent is used to dissolve both the porphyrin and the phospholipid.

Phospholipids are amphophilic in nature, i.e., the molecules have a hydrophobic tail such as a long chain hydrocarbon, and a hydrophilic head. In an aqueous medium, such as water or saline, the tails of the molecules align with each other, away from the aqueous phase, while the heads of the molecules face outward into the aqueous phase. It is this nature of the phospholipids that makes them very useful for formulating soluble compositions from highly insoluble drugs like porphyrins.

The phospholipids used in the invention are preferably selected such that their phase transition temperature is equal to or below the body temperature of about 37° C. and the complex releases the drug in the body. Representative examples of useful phospholipids include the synthetic phospholipids, dimyristoyl phosphatidylcholine (DMPC), dimyristoyl phosphatidyl-glycerol (DMPG), dipalmitoylphosphatidylcholine (DPPC), dipalmitoylphosphatidylglycerol (DPPG), distearoylphosphatidycholine (DSPC), distearoylphosphatidylglycerol (DSPG), or a combination thereof. Other examples of phospholipids can be found in the *CRC Handbook of Lipid Bilayers* by Marsh, M. A., CRC Press (199). When DMPC and DMPG are used in a ratio of DMPC to DMPG of about 7:3 they mimic the cell membrane.

The porphyrin and the phospholipid are added to the solvent such that the weight ratio of the porphyrin to lipid is about 1/10 to 1/100 and preferably about 1/10 to 1/40.

In some applications, it has been found desirable to add cholesterol or its hemisuccinate derivatives or other salt forms to the lipid complex. The cholesterol is believed to slow down the release of the drug. This approach may be particularly desirable with subcutaneous formulations where severe necrosis can result if the drug is delivered too quickly. The cholesterol may be used in amounts up to about 50 parts per hundred parts phospholipid and preferably about 0.5 to 15 parts per 100 parts phospholipid.

Once the lipids and porphyrin have been added to the solvent and thoroughly mixed, water or an aqueous solution is added rapidly to the mixture with stirring for several minutes. Addition of the water is believed to cause the porphyrin and the lipid to come out of solution and complex with each other. The water is preferably added in an amount such that the porphyrin is present in an amount of about 10 mg to 100 mg per 100 ml water. It is desirable to limit the amount of water because higher amounts of water increase the amount of water that must be removed during the subsequent lyophilization process. It is believed that complexation may be complete in about 30 minutes. However, it is desirable to stir the dispersion for about one hour to insure that the complexation is complete.

The lipid complex dispersion described above, is treated to remove the solvents. Any of a variety of techniques can be used for this purpose. For example, it has been found that chloroform can be effectively removed if the dispersion is sparged with an inert gas such as nitrogen.

A pharmaceutically acceptable lyophilization excipient is dissolved in the aqueous phase of the dispersion. Mannitol it typically used as the excipient but other excipients which do not interact with the drug or the lipid complex may be used. Sodium or potassium phosphate, citric acid, tartaric acid, gelatin, and carbohydrates such as lactose, dextrose, dextran, hetastarch, etc. are common examples of excipients which are also believed to be useful herein. The excipients can be used alone or in combination to provide a cake of good quality which readily disperses in water upon reconstitution.

The excipients arc typically added to the dispersion as solutions in water. Again, it is desirable to use concentrated solutions to minimize the amount of water for removal by lyophilization. The amount of the excipient is adjusted in a manner that is well known in the art to provide a cake which does not crack or shrink and is porous so that it readily dissolves and has a good appearance. Mannitol has been found to be particularly useful. Mannitol is added to the dispersion as a solution having a concentration of about 0.01 to 0.15 g/ml. Mannitol is added in an amount of about 1 to 100 parts by weight per part tin porphyrin.

After removing the solvents and adding the excipient, the dispersion is passed through a homogenizer (e.g., a Tekmar rotor/stator homogenizer, Model T25, or a microfluidics submerged jet homogenizer, Model M110Y). As a general rule, the smaller the particle size of the dispersion, the faster the formulation can be dried during the lyophilization cycle. A dispersion having a particle size distribution ranging from about 10 to 4000 nm and averaging about 600 nm has been found to be satisfactory for lyophilization. The optimum particle size may vary depending on the mode of administration.

A typical lyophilization cycle useful in accordance with the present invention is provided below. The cycle may be varied depending upon the equipment and facilities available in a manner well known in the art.

The homogenized formulation can be poured into vials of a 5 to 50 mL nominal volume. The vials are placed into a lyophilization chamber at about 5° C. The vial size will usually be selected such that each vial contains a single dosage of the porphyrin-lipid complex. The temperature of the chamber is reduced to −30° C. over a period of one hour after which the temperature is maintained at −30° C. for about four hours. The pressure in the lyophilization chamber is then reduced to 200–250 microns of pressure for the remainder of the cycle. After reducing the pressure in the chamber, the temperature is ramped up to +25 C. over a period of 15 hours and the product is held at +25° C. for five hours. The temperature then is ramped up to +40° C. over a period of 20 minutes and held at 40° C. for two hours. The lyophilized product preferably has a final moisture content of less than about 5% and typically about 1 to 2%.

The lyophilizate prepared in accordance with the present invention can be reconstituted with water, saline, or another electrolyte or non-electrolyte diluent to give a colloidal dispersion for administraion in a conventional manner such as intravenous or intraperitoneal administration. The lyophilized product with the addition of water provides a colloidal dispersion of the lipid-porphyrin complex in an aqueous solution of the excipient. A colloidal dispersion consists of at least two discrete phases. The first is a dispersed or internal phase; the second is a continuous or external phase. Systems in the colloidal state contain one or more substances that have at least one dimension in the range of 10–100A to a few microns. See pp. 272–4 in Chapter 19, Disperse Systems, *Remington's Pharmaceutical Sciences*, 18th Edition, 1990, Mack Publishing Company, Easton, Pa. 18042. In the colloidal dispersions of the present invention, the dispersed or internal phase comprises particles of the porphyrin/lipid complex having a particle size in the range of 10 nm to 5000 nm. In selecting the aqueous vehicle, it is recommended to use one having a specific gravity about equal to the lipid complex (est. 1.09 g/cc) to minimize the tendency for the dispersion to separate. The lyophilizate of the lipid complex can be reconstituted with water, saline, or another pharmaceutically acceptable aqueous diluent for intravenous administration. Upon reconstitution a dispersion is obtained which is suitable for injection. The lyophilizate can also be administered orally as an aqueous dispersion or as an encapsulated paste. While porphyrins are not generally administered subcutaneously because they cause necrosis, it has been observed that the lipid slows the release of the porphyrin into the tissue making it potentially feasible to administer the lipid-porphyrin complex subcutaneously. The preferred route of administration is intravenous or intraperitoneal.

For oral administration, the lyophilizate can be reconstituted to form an oral dispersion or formulated into a paste. Typically, the lyophilizate is filled into a soft gelatin capsule for oral administration.

Suitable dosages for lipid complexes of tin porphyrin range from about 10 to 200 $mg/m^2/hour$. The drug is preferably administered as a continuous infusion over 0.5 to 5 hours using a programmable continuous infusion ambulatory pump or an IV infusion bag. After administration of the complex to the patient, the patient is exposed to radiation in photodynamic therapy in a known manner. This therapy is normally conducted by exposure to radiation in the range of 300 to 700 nm.

The invention will now be described in more detail with reference to the following non-limiting example.

EXAMPLE 44.8 g of Cholesterol, 162.4 g of dimyristoyl phosphatidylcholine, 72.8 g of dimyristoyl phosphatidylglycol and 9.38 g of α-tocopherol were dissolved in 1.862 liters of chloroform. The purpose of d-tocopherol is to minimize oxidative damage to the molecule. Other antioxidants like BHT (butylated hydroxy toluene) or BHA (butylated hydroxy aninsole) may be used. 9.38 g of tin porphyrin (tin ethyl etioporphyrin) having the structure:

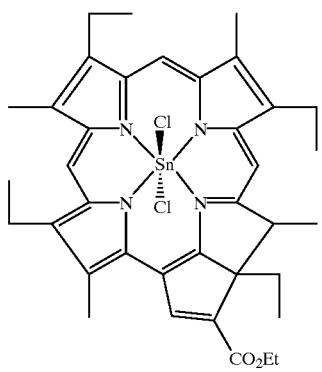

was added to the above solution and stirred for 15 minutes. A volume of water for injection, USP equal to the volume of chloroform used was added to the above solution and stirred vigorously for one hour. The resulting suspension was then sparged using nitrogen until all the chloroform was removed (less than 1000 pp of chloroform remained). To this suspension was added 348.6 g of mannitol dissolved in 3486 mL of water for injection, USP. The resulting product was homogenized using a Microfluidizer, Model 110Y. The resulting lipid/tin porphyrin complex formulation was filled in 50 cc amber, molded vials, 30 mL to a vial, and then freeze-dried.

The freeze-dried product was reconstituted in 20 mL of water for injection, USP. The reconstituted product was stable at room temperature for at least 144 hours, when protected from light.

The stability of the freeze-dried products was evaluated under varying conditions for up to 4 weeks. The results are shown in Table 1 where RS1, RS2, RS3, RS4 refer to HPLC peaks of products associated with degradation of the lyophilizate and "n.d." means "none detected."

TABLE 1

Stability Results: 1 day – 4 weeks

| time | storage conditions | % of initial | RS1 | RS2 | RS3 | RS4 |
|---|---|---|---|---|---|---|
| 1 day | UV control | 99.75% | n.d. | n.d. | n.d. | n.d. |
| 1 day | UV | 101.90% | n.d. | n.d. | n.d. | n.d. |
| 1 day | 100 foot candles | 101.38% | n.d. | n.d. | n.d. | n.d. |
| 1 week | 50° C., 60% humidity | 100.03% | n.d. | n.d. | n.d. | n.d. |
| 2 weeks | 100 foot candles | 97.30% | n.d. | 0.21% | n.d. | n.d. |
| 2 weeks | 5° C. | 100.93% | n.d. | n.d. | n.d. | n.d. |
| 2 weeks | 25° C., 60% humidity | 102.21% | n.d. | n.d. | n.d. | n.d. |
| 2 weeks | 40° C., 80% humidity | 100.52% | n.d. | n.d. | n.d. | n.d. |
| 2 weeks | 50° C., 60% humidity | 99.60 | 0.06% | n.d. | n.d. | n.d. |
| 3 weeks | 5° C. | 100.52% | n.d. | n.d. | n.d. | n.d. |
| 3 weeks | 25° C., 60% humidity | 99.21% | n.d. | n.d. | n.d. | n.d. |
| 3 weeks | 40° C., 80% humidity | 97.02% | n.d. | n.d. | n.d. | n.d. |
| 3 weeks | 50° C., 60% humidity | 98.30% | n.d. | n.d. | 0.44% | n.d. |
| 4 weeks | 100 foot candles | 99.42% | n.d. | n.d. | n.d. | 0.34% |
| 4 weeks | 5° C. | 100.68% | n.d. | n.d. | n.d. | n.d. |
| 4 weeks | 25° C., 60% humidity | 100.67% | n.d. | n.d. | n.d. | n.d. |
| 4 weeks | 40° C., 80% humidity | 98.65% | n.d. | n.d. | n.d. | 0.52% |
| 4 weeks | 50° C., 60% humidity | 99.16% | n.d. | n.d. | 0.84% | n.d. |

| RS | RRT* |
|---|---|
| 1 | .04 |
| 2 | 0.58 |
| 3 | 1.23 |
| 4 | 1.46 |

*Relative Retention Time based on main sn $Et_2$ peak at 8.2 minutes

Having described the invention in detail and by reference to preferred embodiments thereof, it will be apparent that modifications and variations are possible without departing from the scope of the invention defined in the appended claims.

What is claimed is:

1. A pharmaceutical composition comprising a lyophilizate of a complex of a porphyrin, a phospholipid, and a pharmaceutically acceptable lyophilization excipient, wherein the porphyrin has the structure:

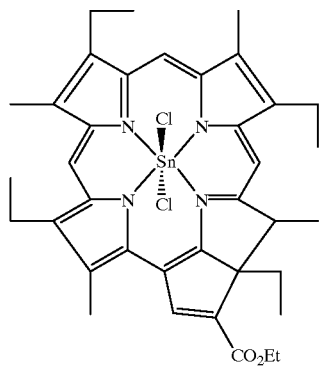

2. The composition of claim 1 wherein said composition forms a colloidal dispersion of the complex when reconstituted with a physiologically acceptable aqueous diluent.

3. The composition of claim 1 wherein said phospholipid is selected from the group consisting of dimyristoylphosphatidylcholine, dimyristoylphosphatidylglycerol, dipalmitoylphosphatidylcholine, dipalmitoylphosphatidylglycerol, distearoylphosphatidylcholine, distearoylphosphatidylglycerol, and mixtures thereof.

4. The composition of claim 3 wherein said phospholipid is a mixture of dimyristoylphosphatidylcholine and dimyristoylphosphatidylglycerol.

5. The composition of claim 4 wherein said dimyristoylphosphatidylcholine is present in a weight ratio to said dimyristoylphosphatidylglycerol of about 7 to 3.

6. The composition of claim 1 wherein the weight ratio of said porphyrin to said phospholipid in said composition is about 1 to 30.

7. The composition of claim 1 wherein said excipient is mannitol.

8. The composition of claim 1 wherein the complex is a lipid complex of the porphyrin and a mixture of dimyristoylphosphatidylcholine and dimyristoylphosphatidylglycerol in a ratio of said porphyrin to said mixture of dimyristoylphosphatidylcholine and dimyristoylphosphatidylglycerol of about 1 to 30, said dimyristoylphosphatidylcholine and said dimyristoylphosphatidylglycerol being present at a weight ratio of about 7 to 3; and a mannitol lyophylization excipient.

9. A method for preparing a lyophilizate of a lipid complex of a porphyrin which comprises the steps of preparing a concentrated solution of a porphyrin and a phospholipid in an organic solvent, adding water to the solution to cause formation of a complex of the porphyrin and the phospholipid, removing the organic solvent to provide a dispersion of the lipid complex in water as an aqueous phase, dissolving a pharmaceutically acceptable excipient in the aqueous phase of the dispersion, and lyophilizing the dispersion of the lipid complex to form a lyophilizate, wherein said porphyrin has the structure:

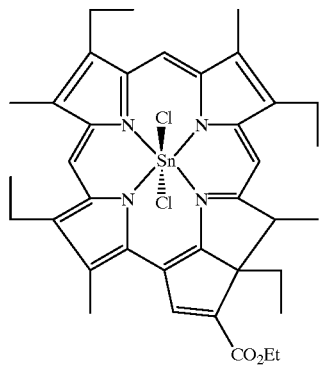

10. The method of claim 9 wherein said phospholipid is selected from the group consisting of dimyristoylphosphatidylcholine, dimyristoylphosphatidylglycerol, dipalmitoylphosphatidylcholine, dipalmitoylphosphatidylglycerol, distearoylphosphatidylcholine, distearoylphosphatidylglycerol, and mixtures thereof.

11. The method of claim 10 wherein said phospholipid is a mixture of dimyristoylphosphatidylcholine and dimyristoylphosphatidylglycerol.

12. The method of claim 11 wherein said dimyristoylphosphatidylcholine is present in weight ratio to said dimyristoylphosphatidylglycerol of about 7 to 3.

13. The method of claim 9 wherein said lyophilization excipient is mannitol.

14. A method of photodynamic therapy comprising the steps of:

administering an effective amount of a lyophilizate of a complex of a porphyrin, a phospholipid, and a pharmaceutically acceptable lyophilization excipient to a patient; and exposing said patient to radiation at a wavelength in the absorption spectrum of said porphyrin, wherein the porphyrin has the structure:

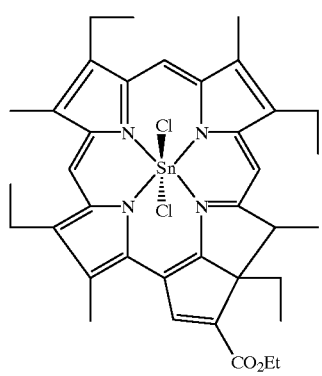

15. The method of claim 14 wherein said step of administering the lipid complex to the patient includes preparing a lyophilizate of the complex and a pharmaceutically acceptable excipient and preparing a colloidal dispersion of the complex in a pharmaceutically acceptable vehicle from the lyophilizate.

16. The method of claim 14 wherein the lyophilizate of a complex is administered as a colloidal dispersion in a pharmaceutically acceptable vehicle.

* * * * *